(12) United States Patent
Boecker et al.

(10) Patent No.: US 9,222,916 B2
(45) Date of Patent: Dec. 29, 2015

(54) THROUGH-COIL ARRANGEMENT, TEST APPARATUS WITH THROUGH-COIL ARRANGEMENT AND TESTING METHOD

(71) Applicant: Institut Dr. Foerster GmbH & Co. KG, Reutlingen (DE)

(72) Inventors: Matthias Boecker, Reutlingen (DE); Franz Haditsch, Reutlingen (DE); Stefan Koch, Bisingen (DE)

(73) Assignee: Institut Dr. Foerster GmbH & Co. KG, Reutlingen (DE)

( * ) Notice: Subject to any disclaimer, the term of this patent is extended or adjusted under 35 U.S.C. 154(b) by 0 days.

(21) Appl. No.: 14/111,121

(22) PCT Filed: Jan. 11, 2013

(86) PCT No.: PCT/EP2013/050470
§ 371 (c)(1),
(2) Date: Nov. 26, 2013

(87) PCT Pub. No.: WO2013/124087
PCT Pub. Date: Aug. 29, 2013

(65) Prior Publication Data
US 2015/0002144 A1 Jan. 1, 2015

(30) Foreign Application Priority Data

Feb. 23, 2012 (DE) .......................... 10 2012 202 800
Dec. 5, 2012 (EP) ...................................... 12195748

(51) Int. Cl.
*G01N 27/90* (2006.01)
(52) U.S. Cl.
CPC ........ *G01N 27/9033* (2013.01); *G01N 27/9026* (2013.01)
(58) Field of Classification Search
CPC .............. G01N 27/902; G01N 27/903; G01N 27/9033; G01N 27/9026
USPC ......................................................... 324/240
See application file for complete search history.

(56) References Cited

U.S. PATENT DOCUMENTS 2,124,579 A 7/1938 Knerr et al.
5,623,203 A * 4/1997 Hosohara et al. ............. 324/220
(Continued)

FOREIGN PATENT DOCUMENTS

AT 502 976 A1 6/2007
DE 80 12 257 U1 10/1980
(Continued)

OTHER PUBLICATIONS

International Search Report dated May 7, 2013 with English translation (six (6) pages), PCT/EP2013/05070.

*Primary Examiner* — Reena Aurora
(74) *Attorney, Agent, or Firm* — Crowell & Moring LLP

(57) ABSTRACT

A feed-through coil arrangement for an apparatus that tests long products via eddy current includes an exciter coil arrangement with an exciter coil having a passage opening for the long product, and a receiver coil arrangement around the opening. The receiver coil arrangement includes two segment coil arrangements distributed over the passage circumference, wherein each segment coil arrangement has a detection range covering only a circumferential section of the long product circumference. The segment coil arrangements are distributed over two shells surrounding the opening at different distances to a reference axis. First segment coil arrangements on a first shell are without reciprocal overlapping and second segment coil arrangements on a second shell are without reciprocal overlapping. The first and second segment coil arrangements are arranged circumferentially offset to one another such that the second segment coil arrangements detect circumferential sections not covered by the first segment coil arrangements.

18 Claims, 6 Drawing Sheets

(56) References Cited

U.S. PATENT DOCUMENTS 6,310,476 B1 * 10/2001 Kawanami et al. ........... 324/241
8,803,515 B2 * 8/2014 Goldfine et al. .............. 324/239
2007/0205764 A1 9/2007 Kroner

FOREIGN PATENT DOCUMENTS

| DE | 44 38 171 A1 | 5/1996 |
| DE | 101 35 660 C1 | 11/2002 |
| GB | 516 753 A | 1/1940 |

* cited by examiner

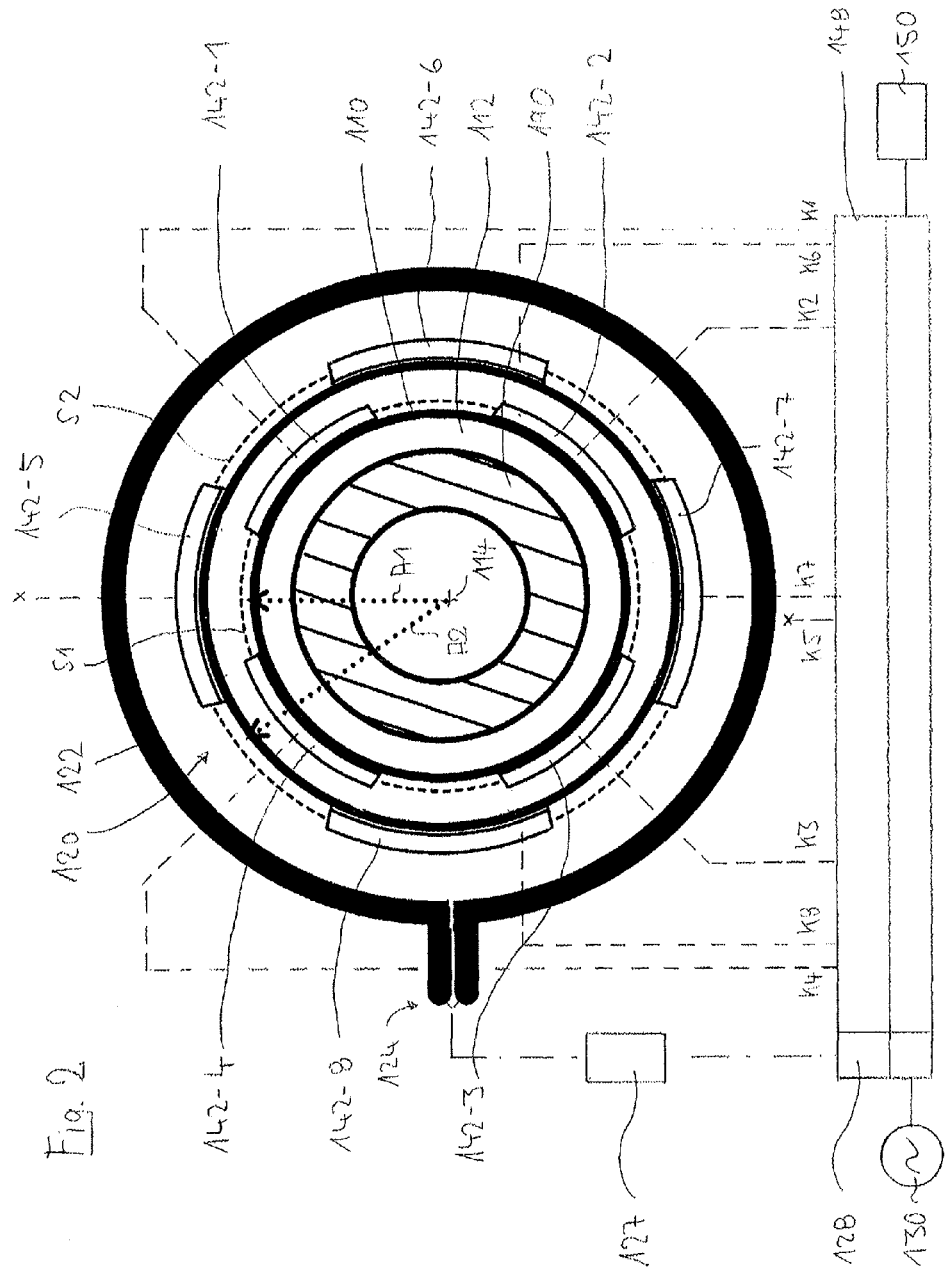

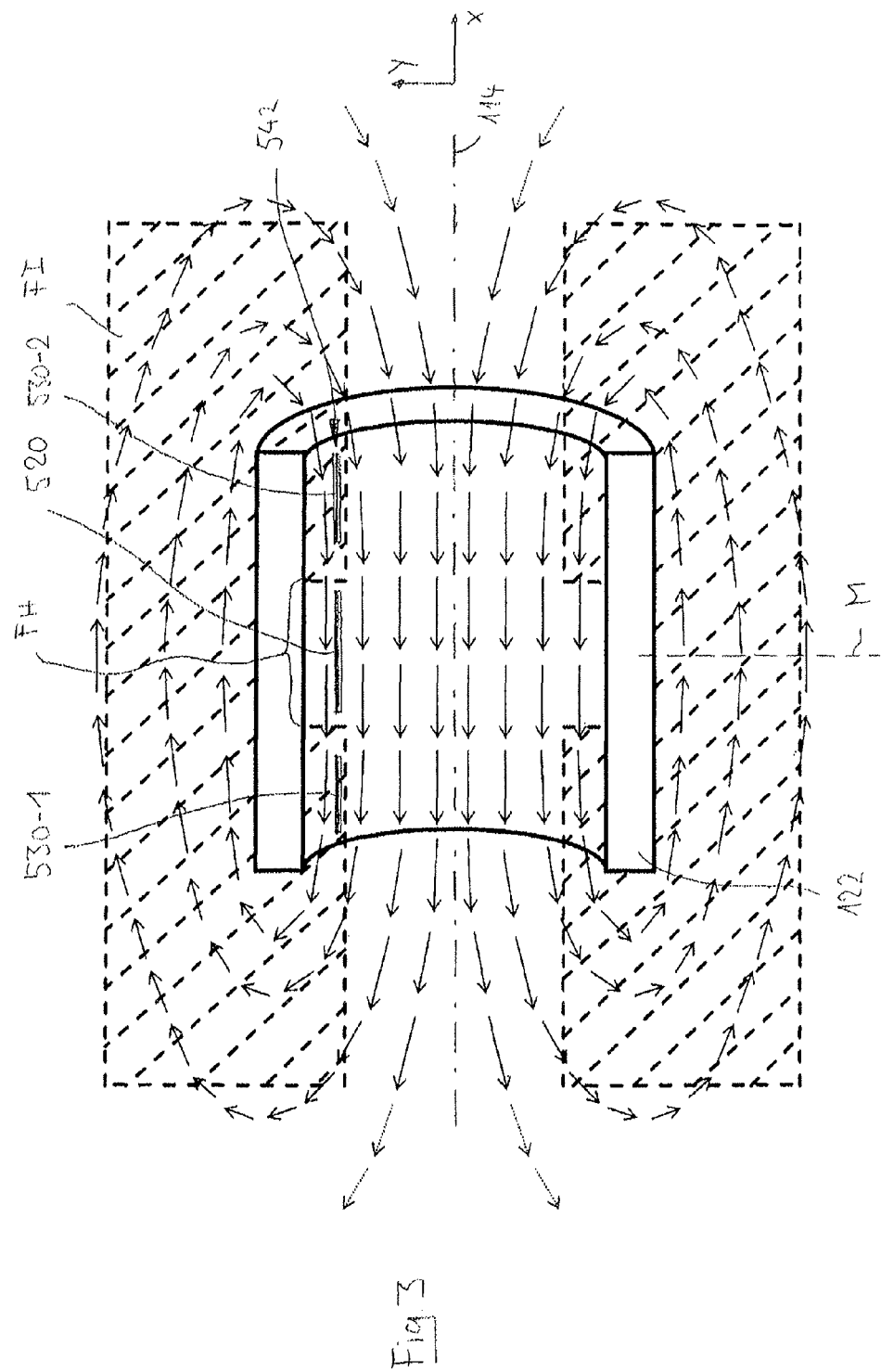

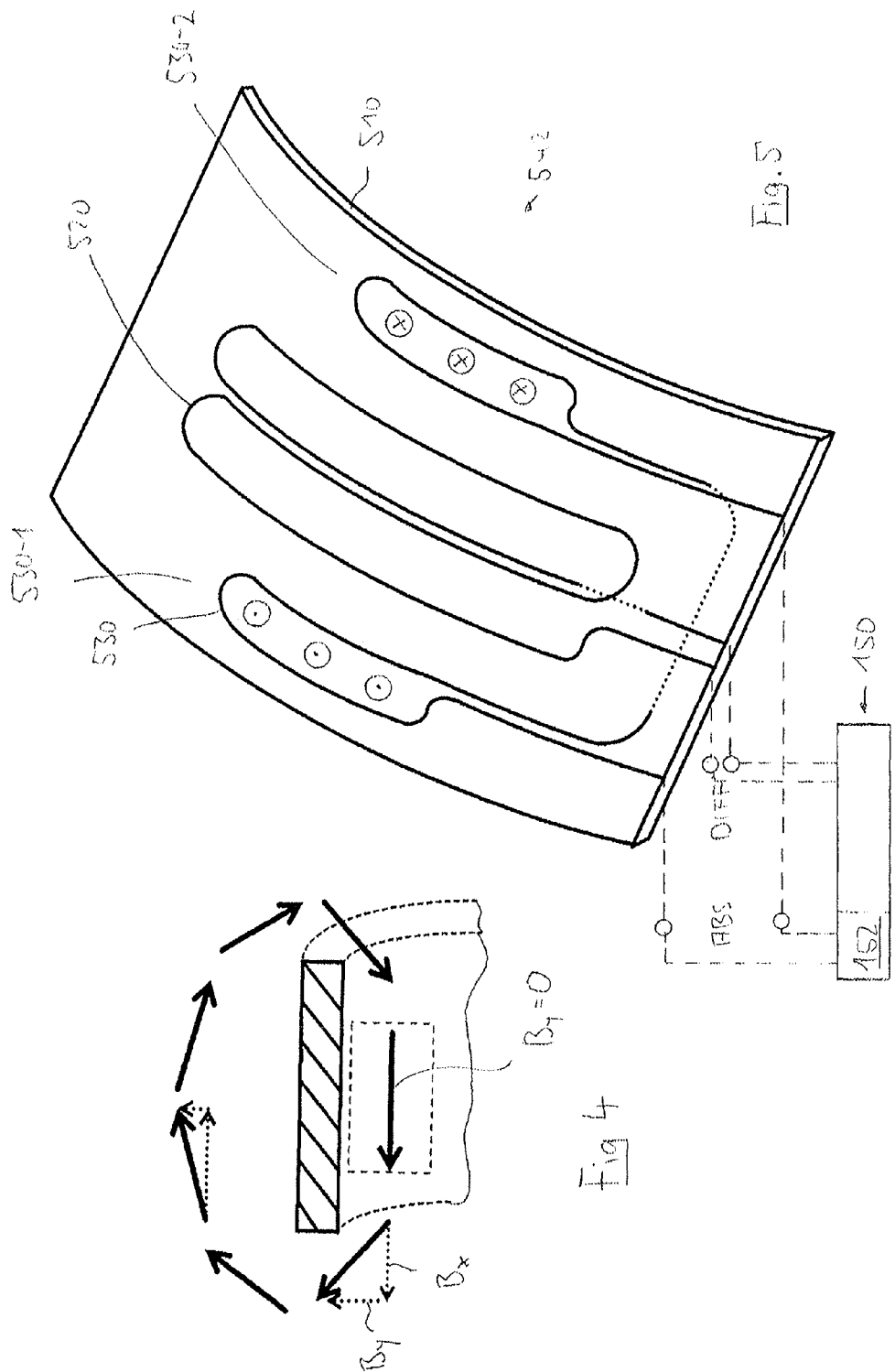

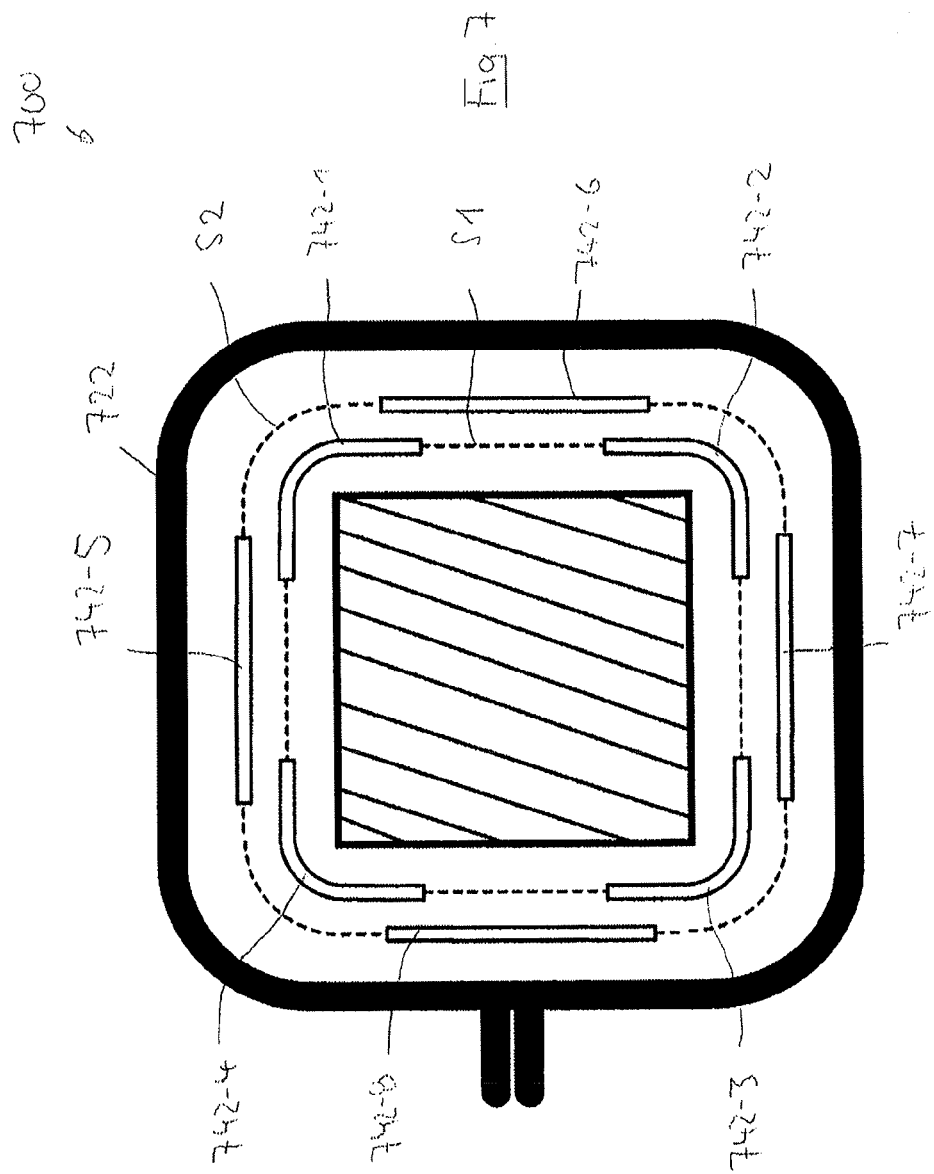

THROUGH-COIL ARRANGEMENT, TEST APPARATUS WITH THROUGH-COIL ARRANGEMENT AND TESTING METHOD

BACKGROUND

1. Field of the Invention

The invention relates to a feed-through coil arrangement for use in a test apparatus for testing long products in a feed-through method by means of eddy current, to a test method for testing long products by means of eddy current as well as to a test apparatus having such a feed-through coil arrangement.

2. Prior Art

Long products are elongated metallic objects, such as wires, bars, rods or tubes or the like, for example. Such long products can serve as starting materials for high quality end products and are frequently subject to extremely high quality requirements. Testing for material flaws or faults, for example for cracks near to the surface, cavities, scabs or other material inhomogeneities (in the following also referred to as flaws or defects), forms an important part of the quality control of these products. In this context, a most complete testing of the material surface with a high resolution is generally aimed at, which testing is to be capable of being carried out where possible at the manufacturing site in synchronism and at the speed of the manufacturing process. Nowadays such tests are often carried out using electromagnetic methods, in particular eddy current technology, in a feed-through method. During a test using a feed-through method, an object to be tested (test specimen, test object) is moved at a predefinable, where required relatively high, feed-through speed through a test section of a test apparatus equipped with the corresponding sensor system, and the object is tested in the process.

During the non-destructive testing of materials using the eddy current method, an exciter coil operated with alternating current is used to induce an electrical alternating current (eddy current) with a suitable orientation, magnitude and frequency in the material to be tested, and the irregularities which are produced in the eddy current are detected and evaluated using sensors, for example a coil arrangement.

In eddy current testing, use is made of the effect according to which most impurities or defects in an electrically conductive material have an electrical conductivity and/or permeability different from that of the test material per se. The measurement signal to be evaluated is determined in particular from the conductivity and permeability of the material of the test specimen and from the distance between the eddy current sensor and the material surface, wherein the absolute strength of the fault signal and also the ratio between the useful signal and interference signals (signal-to-noise ratio, S/N ratio) decrease as the distance of the sensor from the material surface increases.

In one class of test apparatuses for the feed-through method, a feed-through coil arrangement comprising the test object is used through which arrangement the object to be tested (the long product) is fed through. A feed-through coil arrangement comprises an exciter coil arrangement with an exciter coil, which surrounds a passage opening for feeding through an elongated object along a feed-through direction. The exciter coil arrangement comprises a connection device for connecting the exciter coil to an alternating current voltage source. Furthermore, a receiver coil arrangement arranged around the passage opening is provided, which comprises a connection device for connecting the receiver coil arrangement to an evaluation device of the test apparatus. The exciter coil arrangement and the receiver coil arrangement are connected to the electric or electronic components of the test apparatus via the connection devices. Such comprehensive feed-through coil arrangements may generally be produced relatively cost-efficiently and are reliable and efficient in use even under tough environmental conditions due to their robustness.

In the patent specification DE 101 35 660 C1, such a feed-through coil arrangement is described, that would allow economic and reliable detection of path-type faults, to ensure a clear fault resolution and a good reproducibility of the test result. The feed-through coil arrangement comprises a measuring element surrounding the object to be tested externally in the form of at least three segment measuring coils made of strip lines using a differential or multi-differential circuitry surrounding the object circularly at a medium radial distance. Said segment measuring coils overlap in the circumferential direction with their end sections adjacent to one another and are coupled to a multichannel evaluation electronic system. Furthermore, the segment measuring coils are surrounded by an absolute coil, which in turn is surrounded by an exciter coil assigned to all measuring coils. In configurative adaptation to the segment measuring coils, the absolute coil may also be segmented, wherein in that case, the segment absolute coils overlap with their end sections. As a result of the coil effective areas of the segment measuring coils overlapping in the circumferential direction, a real 100% coverage of the surface of the object to be tested at the same sensitivities is to be achieved.

OBJECT AND SOLUTION

It is an object of the invention to provide such a feed-through coil arrangement for use in a test apparatus for testing of long products in the feed-through method, which arrangement is capable of providing meaningful test results about defects and other irregularities in the test object passing through, with an inexpensive and robust structure. It is another object to provide a test method as well as a test apparatus working with such a feed-through coil arrangement.

In order to achieve said objects, a feed-through coil arrangement is provided for use in a test apparatus for testing long products in a feed-through method by use of eddy current, comprising: an exciter coil arrangement with an exciter coil which surrounds a passage opening for feeding-through a long product along a feed-through direction, wherein the exciter coil arrangement comprises a connection device for connecting the exciter coil to an alternating current source; and a receiver coil arrangement arranged around the passage opening, which comprises a connection device for connecting the receiver coil arrangement to an evaluation device of the test apparatus. The receiver coil arrangement comprises two or more segment coil arrangements distributed over the circumference of the passage opening, wherein each segment coil arrangement has a detection range that only covers a circumferential section of the circumference of the surface of the long product. The segment coil arrangements are distributed over at least two shells surrounding the passage opening at different distances to a reference axis of the feed-through coil arrangement, wherein first segment coil arrangements are arranged on a first shell without reciprocal overlapping, second segment coil arrangements are arranged on a second shell without reciprocal overlapping, and first and second segment coil arrangements are arranged circumferentially offset to one another in circumferential direction such that the second segment coil arrangements detect circumferential sections that are not covered by the first segment coil arrangements. Furthermore, a test method as well as a test apparatus are provided.

Advantageous embodiments are indicated in the dependent claims. The wording of all claims is incorporated into the content of the description by reference.

The receiver coil arrangement comprises two or more segment coil arrangements distributed over the circumference of the passage opening. Each of the segment coil arrangements has a detection range covering only part of the entire circumference of the surface of the long product, i.e. a circumferential segment. Such a feed-through coil arrangement includes a common excitation for two or more segment coil arrangements, in each case covering only a part or a segment, respectively of the circumference of the test specimen. Thus, all signals delivered by the individual segment coil arrangements are based on the same excitation and are directly comparable to one another in this respect. At the same time, the segmentation or division, respectively, of the receiver coil arrangement into a plurality of segment coil arrangements allows correlation of occurring fault signals to a certain circumferential section of the object surface. As a result, a localization of defects is not only possible in the longitudinal direction of the object, as in conventional feed-through coil arrangements, but also in circumferential direction. The advantages of conventional feed-through coil arrangements with respect to robustness and reliability can be maintained in this case.

In the invention claimed it is provided that the segment coil arrangements are distributed over at least two shells enclosing the passage opening at different distances to a reference axis of the feed-through coil arrangement. Here, first segment coil arrangements are arranged without reciprocal overlapping in the circumferential direction on a first shell. In contrast, second segment coil arrangements are arranged without reciprocal overlapping in the circumferential direction on a second shell. Since there is a distance between the shells in the radial direction to the reference axis, the first segment coil arrangements have a distance to the reference axis different from that one of the second segment coil arrangements. In this case, the term "shell" refers to a surface extending in the circumferential direction around the reference axis, the surface segments of which surface are aligned parallel to the reference axis and are curved sectionally or continuously in the circumferential direction.

The radial distance of a surface to the reference axis follows a predefined distance function. As a result of the fact that all segment coil arrangements of a shell are located on said shell, the radial distance to the reference axis is exactly defined via the distance function at each point of each segment coil arrangement of a shell. The segment coil arrangements of a shell are arranged on their respective shell without reciprocal overlapping. They can directly adjoin to one another in the circumferential direction. However, generally there is a distance in the circumferential direction between the ends of adjacent segment coil arrangements facing each other.

At a defined distance of the first and the second shell to one another, there is direct comparability of the signals of the first and of the second segment coil arrangement, since the fault signals generated generally show a characteristic distance performance and can thus be compared to one another by means of known distance functions.

The arrangement on two or more shells overlapping in the feed-through direction allows an exact correlation of occurring fault signals to an axial location along the tested long product.

The prevention of reciprocal overlapping in circumferential direction is considered to be advantageous. According to the observations of the inventors, in overlapping regions of segment coil arrangements, which nominally are to be located at the same distance to the reference axis, the distances of the signal generating coil arrangements to the test specimen surface relevant for the test deviate from those outside of the overlapping regions, which may result in measuring inaccuracy. Said inaccuracy is prevented in the case of prevention of reciprocal overlapping.

In order to nevertheless allow a complete testing in the circumferential direction, first and second segment coil arrangements are arranged in the circumferential direction offset to one another such that circumferential sections located between first segment coil arrangements are partially or completely detectable by second segment coil arrangements. In other words: first and second segment coil arrangements are arranged circumferentially offset to one another such that the second segment coil arrangements detect circumferential sections not covered by the first segment coil arrangements. Thus, the first and the second segment coil arrangements cover different circumferential sections of the long product to be tested, wherein the detection ranges complement each other as a whole and partially overlap, where appropriate, such that a complete testing in the circumferential direction is possible.

According to another formulation, the respective segment coil arrangements are arranged on their associated shells without reciprocal overlapping and the respective segment coil arrangements are arranged on the different shells circumferentially offset to one another in the circumferential direction such that the complete circumference is covered by the segment coil arrangements of all shells.

Preferably, segment coil arrangements are distributed over exactly two shells, i.e. one first shell and exactly one second shell. That results in a structure with low complexity from a constructional point of view and it is sufficient to assign the signals generated by the segment coil arrangements to only two distance functions. However, it is also possible to distribute segment coil arrangements over more than two shells, for example over three, four, five or six shells, between which shells in each case a distance is present in radial direction. In this case, it is possible that the complete coverage of the circumference is achieved only by combining segment coil arrangements of three or more shells.

In some embodiments, first segment coil arrangements are arranged on a circular cylindrical first shell at a first radial distance to the reference axis and second segment coil arrangements are arranged on a circular cylindrical second shell at a second radial distance to the reference axis deviating from the first radial distance. If the cross-sectional shape has a central symmetry to a center of symmetry, the axis through the center of symmetry may be referred to as central reference axis or central axis. In such embodiments the shells in each case form circular cylinder shell surfaces coaxially to the central axis of the feed-through coil arrangement. Embodiments with circular cross-section are advantageous for the testing of round material (long product with circular cross-section, solid or tubular), for example, but in the case of suitable signal evaluation, they can also be used for testing of long products having a polygonal cross-section.

In the case of alternative embodiments, the shells may have a cross-sectional shape other than the circular shape. For example, shells having an oval cross-section or an egg-shaped cross-section are possible. It is also possible that the shells have a polygonal cross-section, for example an essentially square-shaped cross-section with rounded corner regions.

The radial distance between the shells and to the reference axis does not have to be uniform but may vary in the circumferential direction.

In order to prevent excessive sensitivity differences between segment coil arrangements, a radial distance between the first shell and the second shell or between adjacent shells, respectively, should be not greater than one centimeter, wherein the distance should preferably be 1 mm or less, in particular between 0.1 mm and 1 mm. Greater distances are possible, signal strength differences can then be counterbalanced or considered, respectively electronically or in a calculative manner.

The number of segment coil arrangements per shell may be adapted to the testing task. It is possible that the number of segment coil arrangements is identical on each shell. Different numbers of segment coil arrangements may also be provided on the shells.

Frequently, it is of advantage if an even number of segment coil arrangements is arranged on a shell, for example two, four, six or eight segment coil arrangements. As an alternative or additionally, a pair or a plurality of pairs of diametrically opposed segment coil arrangements may be provided on a shell. That may apply to individual shells, a plurality of shells or all shells.

Generally, the receiver coil arrangement may comprise a plurality of pairs of diametrically opposed segment coil arrangements. That may result in advantages in the signal evaluation. That measure may be advantageous in the case of feed-through coil arrangements having a shell structure (according to the invention as claimed) or in the case of such feed-through arrangements without shell structure.

Adapted to the respective purpose of use, different embodiments of segment coil arrangements are possible. A segment coil arrangement may comprise exclusively one or a plurality of differential coil arrangements, exclusively one or a plurality of absolute coil arrangements or a combination of at least one differential coil arrangement and at least one absolute coil arrangement.

Here, the term "differential coil arrangement" is to comprise both single differential coil arrangements and multi differential coil arrangements. The electric signals generated by a differential coil arrangement are typically referred to as differential signals.

An absolute coil arrangement delivers absolute signals. In the case of a corresponding evaluation, said signals may be used for flaw detection. Since the amplitude of absolute signals depends strongly and in a characteristic manner on the distance between the absolute coil arrangement and the test specimen surface, an absolute coil arrangement can serve as a distance sensor in the case of a corresponding evaluation of the absolute signals, if said arrangement is connected for operation to a distance evaluation device and the distance signals are evaluated as distance signals accordingly (see e.g. DE 44 38 171 A1).

Preferably, all segment coil arrangements have in each case at least one differential coil arrangement. The term "differential coil arrangement" refers to a coil arrangement which comprises two or more partial coil arrangements acting in opposite manner. As a result, a change in the magnetic field reaching through a differential coil arrangement generates a signal only in the case that the field strength change in the oppositely-acting partial coil arrangements is different. In contrast, if field changes are not present or if the field changes act equally strong in the oppositely-acting partial coil arrangements, there will be no output signal. By means of differential coil arrangements, a very sensitive flaw detection is possible even in case of small flaw dimensions. Differential coil arrangements are preferably arranged such that differential signals can be detected at the entire circumference of the test specimen, so that a complete testing by means of differential coil arrangements is possible in circumferential direction.

Preferably, besides a differential coil arrangement, a segment coil arrangement additionally comprises an absolute coil arrangement. That may be provided for all segment coil arrangements or only for a part of the segment coil arrangements. Here, the term "absolute coil arrangement" refers to a coil arrangement, which delivers an output signal (absolute signal) in the case of a change of the magnetic field reaching through. An absolute coil arrangement may comprise a plurality of partial coil arrangements. However, in contrast to a differential coil arrangement, said partial coil arrangements are connected so as to be concordant with respect to the magnetic field reaching through, so that also a field change in a plurality of partial coil arrangements generates in each case a signal, wherein said signals sum up at the output of the absolute coil arrangement.

Said measure can be advantageous in feed-through coil arrangements having a shell structure (according to the invention as claimed) and in generic feed-through coil arrangements without shell structure.

By means of a differential coil arrangement, e.g. hole defects or transverse defects can be detected with high sensitivity. Furthermore, longitudinal defects can be assessed in accordance with their depth gradient. By means of an absolute coil arrangement, it is possible, inter alia, to detect constant longitudinal faults in their full length. The simultaneous detection of differential signals and absolute signals allows a reliable qualification of the defect types.

Furthermore, by means of an absolute coil arrangement, also distance signals are detectable, so that information on the distance between the segment coil arrangements and the test specimen surface, i.e. the test distance, can be derived from signal portions of the absolute coil arrangement. Said distance signals may for example be used for distance compensation on the electronic side or by means of software, in order to improve the comparability of fault signals detected on different segments in the case of an eccentric test specimen position, for example.

Preferably, a differential coil arrangement and an absolute coil arrangement are arranged on a common support element. As a result, the relative position of said coil arrangements to one another can be set mechanically exact. In some embodiments, the support element has an inner surface (facing towards the test object being fed through) and an outer surface, wherein a differential coil arrangement and an absolute coil arrangement are arranged at least partially at the same surface of the support element. Those parts of the coil arrangements that are arranged at the same surface, have the same distance to the reference axis of the feed-through coil arrangement predetermined by the shape of the shell, so that a common evaluation of the signals is readily possible.

Said measure can be advantageous in feed-through coil arrangements having a shell structure (according to the invention as claimed) and in generic feed-through coil arrangements without shell structure.

In some feed-through coil arrangements, it is provided that in a segment coil arrangement, the differential coil arrangement is arranged essentially symmetrically to a coil plane (typically central plane) of the exciter coil arrangement and the absolute coil arrangement is arranged non-symmetrically to the coil plane partially or completely in an inhomogeneous field region of the field generated by the exciter coil arrangement. As a result, a particularly sensitive distance detection is possible by means of the absolute coil arrangement. In this case, it is to be considered that the windings of the absolute coil arrangement are typically located in a curved area perpendicular to the coil plane of the exciter coil. In the case of the asymmetric arrangement, at least a part of the signal-generating windings are located in the inhomogeneous field region, where the magnetic field occurring at the location of the absolute coil arrangement has a radial component (y-component), which reaches through the absolute coil arrangement. The strength of said component changes significantly depending on the distance between the absolute coil arrangement and the surface of the long product, which influences the field line distribution at the location of the absolute coil arrangement. That results in an arrangement of absolute windings in the gradient field, which arrangement changes in response to radial positional changes of the long product when being fed through. A non-centered or eccentric position of the long product, respectively, results in a change of the magnetic flux through the windings of the absolute coil arrangement, which can be detected by the absolute coil arrangements used as distance sensors.

In some embodiments, a particularly strong and stable distance signal is obtained in that an absolute coil arrangement symmetrically to a coil plane or a central plane of the exciter coil arrangement, respectively, comprises a first partial coil arrangement in a first inhomogeneous field region in front of the coil plane and a second partial coil arrangement in a second inhomogeneous field region behind the coil plane, wherein the first and the second partial coil arrangements are connected as to act in opposite directions. The inhomogeneous field reaches through the partial coil arrangements in different field line directions. By means of being connected in opposite directions, it is achieved that the voltages induced in the partial coil arrangements add up so that strong distance signals are obtained.

The segmentation of absolute coil arrangements used as distance sensors in conjunction with the arrangement in the inhomogeneous part of the magnetic field results in segmented distance detection sensors, which, in contrast to conventional absolute coil arrangements, do not use the field lines running approximately in the feed-through direction of the long product to be tested but the components of the magnetic field lines perpendicular thereto. By means of said magnetic field lines, the change of the gradient field is detected in response to the position of the long product to be tested.

Said measures can be advantageous in feed-through coil arrangements having a shell structure (according to the invention as claimed) and in generic feed-through coil arrangements without shell structure.

The option given by means of the segmentation to generate distance signals separately at different circumferential sections by means of the absolute coil arrangements allows obtaining location information with respect to the position of the long product within the feed-through coil arrangement due to the distance signals.

A common evaluation of absolute signals of pairwise diametrically opposite segment coil arrangements allows, for example, in a particular simple manner the detection of the test specimen diameter in the corresponding diagonal direction and, as the case may be, also of diameter fluctuations and/or misalignments.

Said measures can be advantageous in feed-through coil arrangements having a shell structure (according to the invention as claimed) and in generic feed-through coil arrangements without shell structure.

The invention also relates to a test method for testing long products, where a long product is used along a feed-through direction through a feed-through coil arrangement of the type described in the present invention.

Such feed-through arrangements allow evaluation methods that cannot be conducted with conventional feed-through coil arrangements.

In some embodiments, for example, a common evaluation of signals of pairwise diametrically opposite segment coil arrangements takes place.

In one variant, the common evaluation comprises the detection of a summation signal and/or of a differential signal of distance signals and absolute signals, respectively, of the pairwise diametrically opposite segment coil arrangements. Both the diameter and the eccentricity can be determined by means of the evaluation.

By means of evaluation of distance signals of a plurality (e.g. three, four, five or six) circumferentially offset absolute coil arrangements, inter alia, a determination of diameter values, diameter fluctuations and/or decentrations of the test specimen relative to the feed-through coil arrangement is possible.

In some embodiments, information on diameter, test specimen geometry, out-of-roundness and/or axis offset between the feed-through coil arrangement and the test object is obtained from absolute signals of a plurality of absolute coil arrangements distributed over the circumference.

Another advantage of the use of the invention is that a fault protocol can be generated which includes a correlation between a fault signal and a corresponding circumference section of the object tested. Said information allows a significantly improved and more precise assessment of defects. For example, if a defect that could in principle be reworked is located in a circumference section that will not be stressed in a critical manner during the later use, reworking can be omitted. If reworking is required, the defective region is narrowed down to a relatively small circumferential section based on the fault protocol, so that the faults may easier be found. In the case of faults that cannot be reworked, it can be decided based on the fault protocol whether said faults are located in a critical or in an uncritical circumferential section, so that it can be decided more precisely than before about the further use of the test specimen. That may be reasonable for example in the case of welded tubes for differentiated assessment of seam and wall defects and in the case of polygonal profiles for adequate assessment of edge and face defects. The differentiations and their weighing are particularly important in order to be able to interrupt a production process in due time in order to produce material to be manufactured in a flaw-less quality.

The fault protocol may also include data on diameter, test specimen geometry and/or out-of-roundness of the test object as a function of the position in the longitudinal direction.

In conjunction with the shell structure of the feed-through coil arrangement, particularly precise test results can be achieved. Generally, said measures can advantageously be used in feed-through coil arrangements having a shell structure (according to the invention as claimed) and partially also in generic feed-through coil arrangements without shell structure.

Said features and further features arise not just from the claims but from the description and the drawings, wherein the individual features can be realized in each case on their own or in the form of sub-combinations in an embodiment of the invention and on other fields and can represent embodiments that are advantageous as well as protectable per se. Exemplary embodiments of the invention are illustrated in the drawings and will subsequently be explained in more detail.

BRIEF DESCRIPTION OF THE DRAWING FIGURES

FIG. 2 shows a schematic axial view of the feed-through coil arrangement of FIG. 1;

FIG. 3 shows a longitudinal section through a circular cylindrically shaped exciter coil having symbols regarding the orientation of the magnetic field lines;

FIG. 4 shows details on the field course around an exciter coil;

FIG. 5 shows an inclined perspective view of an embodiment of a segment coil arrangement;

FIG. 7 shows an embodiment of a feed-through coil arrangement having an approximately square-type cross-sectional shape.

DETAILED DESCRIPTION OF PREFERRED EMBODIMENTS

Figure 1:
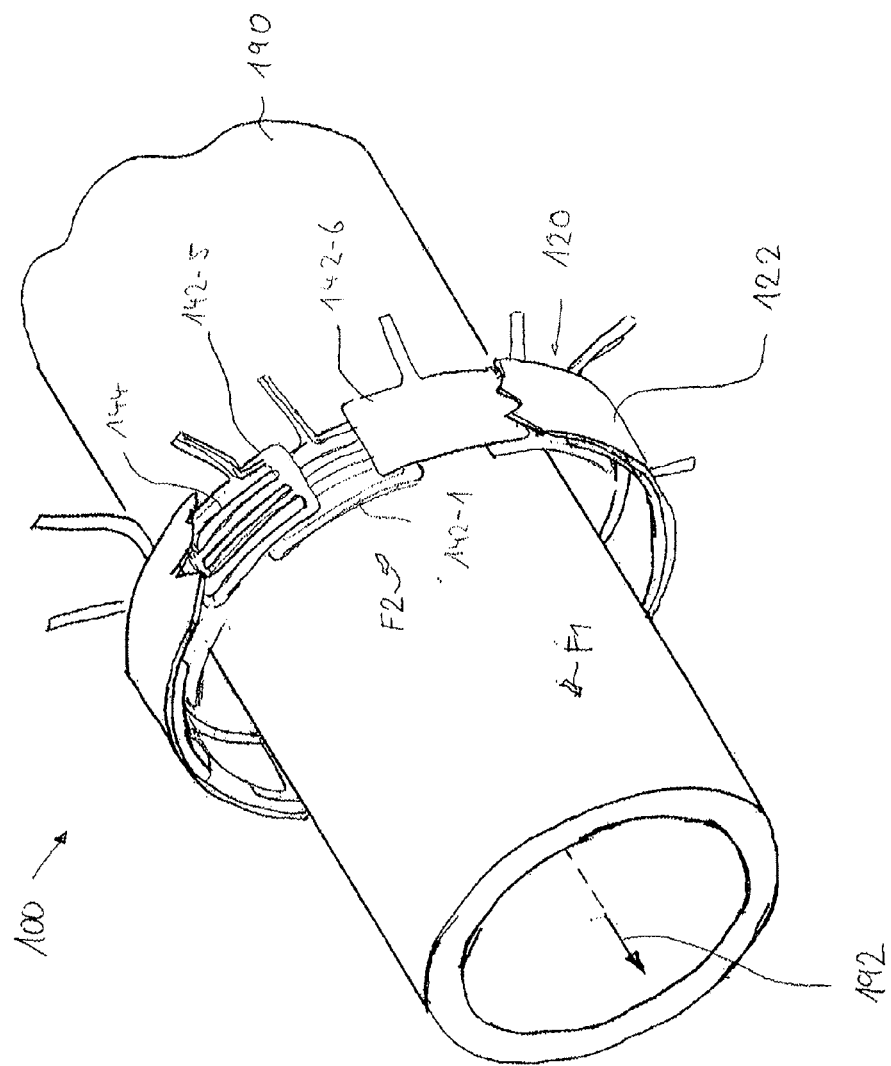
FIG. 1 shows an inclined perspective view of an embodiment of a feed-through coil arrangement according to the invention with a test object being fed through the passage opening.

The schematic inclined perspective view in FIG. 1 shows components of a test apparatus for non-destructive eddy current testing of elongated electrically conductive objects or long products, respectively, in a feed-through method. In the example shown, the object to be tested (test object, test specimen) is a metal tube 190, which is moved along a feed-through direction 192 through a test section of the test apparatus at a feed-through speed up into the range of several meters per second (m/s). The test apparatus may in this case be integrated in a production line, for example a tube weld line. It is also possible that the test apparatus is positioned in a separate test line, which includes a test path that ensures the optimum transport of the test material through the test section. Inter alia, the test path includes guide elements and positioning elements in order to ensure that the central longitudinal axis of the test object extends most centrically through the test section.

A stationary feed-through coil arrangement 100 is arranged in the test section. Said arrangement comprises a coil support 110 shown in FIG. 2, which is essentially produced of a cylindrical sleeve made of an electrically non-conductive or only slightly-conductive material, for example of fiber-reinforced plastic material. The coil support closed in the circumferential direction encloses a circular passage opening 112 for feeding-through the object 190 to be tested. The central axis 114 of the feed-through coil arrangement, which serves as a reference axis, extends in the center of the passage opening. The internal diameter of the coil support is greater than the outer diameter of the greatest test specimen to be fed through by several percent, so that a direct contact between the test specimen and the feed-through coil arrangement is prevented in the case of all test objects to be tested by means of said feed-through coil arrangement.

At the external face of the coil support, the electric components of the feed-through coil arrangement are attached, namely an exciter coil arrangement and a receiver coil arrangement. The exciter coil arrangement 120 comprises one single exciter coil in the form of a flat ribbon coil 122. Said coil is formed by a flat metallic ribbon made of an electrically well-conductive material, for example of copper, which is bent in an annular shape around the coil support or the passage opening, respectively, and has two connection sections 124 radially bent outwards, between which is arranged an insulation layer made of electrically insulating material. The flat ribbon coil forms a single winding which is practically closed over its entire circumference (except for the region of the insulation layer). The coil plane of the exciter coil extends perpendicularly to the central axis 114. The thickness of the flat ribbon measured in the radial direction of the flat ribbon can, for example, be between 0.5 mm and 1 mm and is significantly smaller than the width of the flat ribbon measured parallel to the central axis 114 of the feed-through coil arrangement, which width can range from several millimeters to several centimeters depending on the diameter. For example, the width can be more than 10% of the free internal diameter of the flat ribbon coil and in the exemplary case is approximately 15% of said free diameter. The two ends of the flat ribbon coil are connected to a connection device 128 via conductors illustrated by means of a dot and dash line, via which device the exciter coil arrangement may be connected to an alternating current voltage source 130 of the test apparatus. For adjustment of the impedances of the exciter element 122 and the alternating current voltage source 130, a transformer 127 can be interconnected. The exciter coil arrangement may be operated with a single exciter frequency or with a plurality of different exciter frequencies.

Furthermore, inside the exciter coil arrangement coaxially thereto a receiver coil arrangement arranged around the passage opening 112 is provided, to which receiver coil belongs a connection element 148 for connection of the receiver coil arrangement to an evaluation device 150 of the test apparatus.

In this example, the receiver coil arrangement comprises eight segment coil arrangements 142-1 to 142-8 distributed over the circumference of the passage opening, which arrangements are divided into two groups of in each case four segment coil arrangements. Four first segment coil arrangements 142-1 to 142-4 are located at a first radial distance A1 to the central axis 114 of the feed-through coil arrangement without reciprocal overlapping on a circular cylindrical first shell S1. Four second segment coil arrangements 142-5 to 142-8 are located at a second radial distance A2, which is greater than the first radial distance A1, without reciprocal overlapping on a second shell S2 between the first shell S1 and the exciter shell 122.

The difference of the distances A1 and A2 or the radial distance between the shells, respectively, should be as small as possible, so that the signals detected on different shells can have a most similar signal strength. The radial distance between the shells should be at most one centimeter, if possible, preferably 1 mm or smaller, for example between 0.1 mm and 1 mm. The lower limit of the distance primarily depends on production.

Each of the first segment coil arrangements uniformly distributed on the first shell has a detection range that covers only a circumferential section of approximately 50° of the circumference of the surface of the object to be tested. Gaps remain between the first segment coil arrangements in the circumferential direction. Also the second segment coil arrangements located further outside cover in each case only a circumferential section of approximately 50° of the test specimen circumference and are spaced apart from one another in the circumferential direction. The second segment coil arrangements are arranged circumferentially offset relative to the first segment coil arrangements such that the second segment coil arrangements 142-5 to 142-8 in each case completely cover the gaps existing between the first segment coil arrangements and even overlap with both end segments over the nearest adjacent end sections of the associated first segment coil arrangements 142-1 to 142-4. As a result, the segment coil arrangements distributed over two shells commonly form a closed ring around the passage opening 112 in the circumferential direction.

Each of the segment coil arrangements is connected to the evaluation device 150 via a distinct channel K1 to K8 and the multichannel connection device 148, so that a separate evaluation of the test signals of all segment coil arrangements is possible.

In this "shell model", the windings or coils of the segment coil arrangements located on a common shell are always located at exactly and completely the same radial distance to the central axis, i.e. at the same radius. In segment coil arrangements having different layers, the radial center of the effective region is located on the same radius. All winding regions of segment coil arrangements of the same shell thus have the same sensitivity due to the geometrical arrangement, whereby a direct comparability of the sensor signals is achieved. Here, the shell model eliminates a so far disregarded problem, which may occur in such solutions where segment coil arrangements located on a common radius overlap reciprocally with their end regions. In a distance performance of several dB per millimeter distance in the fault analysis, deviations of more than 1 dB can occur in conventional solutions with reciprocal overlapping. Interpretability of the measuring signals is impaired thereby. Such critical overlappings are prevented.

In the shell model, the segment coil arrangements of the different shells have sensitivity differences due to the distance difference A2–A1. Within a shell, however, there are no sensitivity differences due to the prevention of reciprocal overlapping. As a result of the knowledge of the distance performance of the sensitivity of the segment coil arrangements, said sensitivity differences can be resolved electronically or by means of suitable evaluation software.

The segment coil arrangements are in each case formed as flat coil arrangements meaning that the lateral extension of a coil arrangement in a cylindrically curved surface is significantly greater than the extension measured perpendicularly to said surface. Here, the coils are formed by conductor tracks 144 produced in printed circuit technology, which were applied to a flexible, electrically non-conductive support material (see FIG. 5). During the production of the feed-through coil arrangement, the supports of the inner (first) segment coil arrangements provided with conductor tracks are directly laid onto the cylindrically curved outer face of the coil support 110 and fixed there, for example by means of an adhesive. The outer (second) segment coil arrangements can directly be applied thereon with their support in order to achieve a most small radial distance of the shells. It is also possible to arrange coil supports having a radial distance to one another.

The connection ends of the conductor tracks extend in each case insulated to one another on a narrow integral connection strip which can be connected to the connection element 148 by means of suitable cables. Between the coils of the segment coil arrangements 142-1 to 142-8 and the connection unit 148, amplifier units may be inserted which intensify the signals and/or cause a decoupling of the inductive coil impedance from the mainly capacitive cable impedance.

In the assembled feed-through coil arrangement, the segment coil arrangements are located between the coil support 110 and the external exciter coil 122. There is a radial test distance between the outer face of the test object and the respective segment coil arrangement, which distance is identical for all segment coil arrangements of the same shell in the exemplary case of a circular cylindrical test object, if the test object is fed through the feed-through coil arrangement centrically.

Each segment coil arrangement 142-1 to 142-8 comprises a differential coil arrangement as well as an absolute coil arrangement. As a result, for each circumferential section both a differential signal and an absolute signal can be detected and assigned to the respective circumferential section. By means of a differential coil arrangement, even small defects or other inhomogeneities in an, apart from that, electrically conductive starting material can be reliably detected, since by means of axial differentiation of coil sections, signal parts not tracing back to defects can be largely compensated. As a result of the segmentation, a location resolution/detection is possible in the circumferential direction. For example, the crack-type defect F1 at the circumference of the tube 190 generates a fault signal only in the segment coil arrangement 142-6 of the second shell S2, since the movement path of said fault only passes through the detection range of said one segment coil arrangement while the test object is fed through the system. In contrast, the second fault F2 offset in the circumferential and axial direction generates a fault signal in the circumferentially offset arranged segment coil arrangement 142-1 of the inner first shell at a later point of time. Thus, the two faults can be located in both the axial direction and the circumferential direction. The corresponding fault signals are transmitted to the evaluation unit 150 by means of channels that are separated from one another and can there be correlated to the respective circumferential sections.

By means of the absolute coil arrangement of a segment coil arrangement, serious faults extending predominantly in the longitudinal direction may be detected as a fault signal. Here, however, the option of use as a distance sensor is of particular importance. The signal strength of the absolute signal depends on the distance between the absolute coil arrangement and the material surface in a sensitive manner, wherein the absolute strength of the signal and the ratio between use signal and interference signal decreases as the distance of the absolute coil arrangement from the material surface increases. Over a certain distance range, said relationship is essentially linear and may be calibrated in such a good manner that absolute coil arrangements may also be used as distance sensors.

The distance sensors formed by the absolute coil arrangements are arranged perpendicularly to the feed-through direction in the same plane as the differential coil arrangements by means of which the fault signals may be detected. The evaluation device 150 comprises a distance evaluation device and is configured such that the distance information that can be derived from the signals of the absolute coil arrangement can be further processed for various evaluation purposes.

In the exemplary embodiment, the absolute signals or the distance signals, respectively, of the absolute coil arrangements of the individual segment coil arrangements may one-to-one be assigned to the differential signals of the differential coil arrangement of the respective segment coil arrangement. However, that is not mandatory. It is possible, for example, to evaluate absolute signals in terms of distance information only from a smaller number of selected absolute coil arrangements. It may be sufficient, for example, if only four distance signals from four different (e.g. pairwise opposite) absolute coil arrangements are detected, which are then considered in a software controlled manner in the processing of the differential signals of all eight differential coil arrangements.

FIGS. 3 to 6 explain how to use segmented absolute coil arrangements in order to generate distance signals in embodiments of the invention. For that purpose, FIG. 3 shows a longitudinal section through a circular cylindrically shaped exciter coil 122 parallel to the central axis 114 or to the feed-through direction of a long product to be tested. The exciter coil forms an electrical conductor flown through by an alternating current in the circumferential direction, which generates an alternating electromagnetic field, the magnetic field lines (arrows) of which extend essentially perpendicular to the current flow direction around the exciter coil. Here, symmetrically around the axial central plane M of the exciter coil and symmetrically to the centric coil plane, respectively, an essentially homogeneous field region FH develops, in which the magnetic field lines extends mostly parallel to the feed-through direction or perpendicular to the coil plane of the exciter coil. Towards both axial ends, an inhomogeneous field region FI adjoins to the homogeneous field region FH, in which inhomogeneous region the field of the magnetic field lines is inhomogeneous such that the field lines do not extend parallel to one another and parallel to the central axis.

In the vicinity of the axial ends of the exciter coil as well as in the reflux region of the field lines outside the exciter coil, the magnetic field B does not only have an x-component parallel to the central axis of the exciter coil, but also a finite y-component in the radial direction to the central axis. FIG. 4 schematically shows the components $B_x$ and $B_y$ of the magnetic field. In FIG. 3, the inhomogeneous field region which partially reaches up to the interior of the exciter coil and includes the outer reflux region, is emphasized with dashes. The homogeneous field region is shown without haching. The inhomogeneous field region is conceivable for the positioning of an absolute coil arrangement for distance compensation.

In embodiments of the invention, segmented absolute coil arrangements are used as distance sensors, which not in conventional manner use those field lines that extend parallel to the feed-through direction of the long product to be tested, but the components of the magnetic field lines perpendicular thereto, i.e. the y-components. In that case, use is made of the fact that depending on the position of the long product to be tested, changes of the absolute field and of the gradient field arise that can be detected in the inhomogeneous field region. Here, essentially the primary magnetic field generated by the exciter coil is detected, which, however, is interfered with and reduced by eddy current magnetic fields in the long product. Measuring is not effected in the almost homogeneous region FH, but in the inhomogeneous reflux region where there is no homogeneous field but a gradient field which can change as a result of the eccentricity of the long product to be tested. One reason is the proximity effect, which generates different eddy currents in response to the eccentricity of the long product and thus also influences the magnetic field lines in the reflux region.

In conventional, all-embracing absolute coils, which surround the long product to be tested, said effects predominantly cancel each other within the coil, so that possibly resulting signals do not allow any usable conclusion regarding a possible eccentricity of the long product being fed through. In contrast, in embodiments of the invention, changes in the gradient field can be detected and processed in the form of distance signals.

To that end, FIG. 5 shows an oblique perspective, schematic view of an embodiment of a segment coil arrangement 542 which is arranged on one of the shells of the feed-through coil arrangement. On a cylindrically curved, electrically insulating support element 510, a differential coil arrangement 520 and an absolute coil arrangement 530 are arranged electrically insulated from one another. The absolute coil arrangement includes a first partial coil arrangement 530-1 on an axial side of the differential coil arrangement and a second partial coil arrangement 530-2 on the opposite axial side. The windings of the two partial coil arrangements are connected to one another having opposite directions.

FIG. 3 shows the installation situation of the segment coil arrangement 542 inside the exciter coil 122. It can be seen that the segment coil arrangement with respect to the coil plane of the exciter coil arrangement (central plane M) in the installed state is arranged such that the differential coil arrangement 520 is located symmetrically to the coil plane in the homogeneous field region FH of the exciter coil. In contrast, the partial coil arrangements of the absolute coil arrangement which adjoining the axial ends are located in the inhomogeneous field region FI already, so that the coil surface defined by the windings of the partial coil arrangements is penetrated by the y-components of the magnetic field lines extending radially to the central axis.

Here, decisive for the performing of the absolute coil arrangement as distance sensor is that the two partial coil arrangements 530-1 and 530-2 are penetrated by the inhomogeneous field in different field line directions (see circular field symbols in FIG. 5). Here, the y-components of the B-field induce voltages. A series connection of the partial coil arrangements would result in a partial or a complete cancellation of the voltages induced in the coils. In contrast, by means of connecting in opposite direction it is achieved that the voltages induced in the two partial coil arrangements add up so that based on the changes of the gradient field, a strong absolute signal ABS results. An additional advantage of said construction of the absolute coil arrangement symmetrically to the central plane M of the exciter coil is that a negative influence is not exerted to the flaw detection.

In a completely assembled test apparatus, the absolute coil arrangement 530 is connected to a distance evaluation unit 152 integrated in the evaluation device 150.

A difference signal DIFF is present at the connection end of the differential coil arrangement 520. Said signal is also evaluated in the evaluation unit 150.

During the introduction of a long product and related generation of a secondary magnetic field due to the eddy currents developing in the long product, the field line distribution changes. In the case of a centric position of the long product relative to the central axis of the feed-through coil arrangement, the field line displacement would be identical in all locations. In contrast, in the case of a non-centric position of the long product, a non-symmetric field line distribution arises, which can be detected by the absolute coil arrangements acting as distance sensors.

In this embodiment, the absolute coil arrangement is formed by windings, which at first sight seem to have a difference sensor character. However, due to the different penetration directions of the field lines used, an absolute coil character arises, whereby a new type of distance sensor is realized.

As an alternative to the visually shown arrangement with two partial coil arrangements of the absolute coil arrangement symmetric to the coil plane, it is also possible to attach an absolute coil arrangement only on one side of the differential coil arrangement (inlet or outlet side of the feed-through coil arrangement), which absolute coil arrangement uses the components of the magnetic field lines extending in the radial direction for signal generation.

An absolute coil arrangement may also be located in the outer reflux region of the field of the exciter coil (see hatching).

The windings of the absolute coil arrangement can be located on a common cylindrical surface, i.e. on the same radius. It is also possible, that parts of the absolute coil arrangement are located at different radial distances to the central axis. The form of the loops or windings, respectively, can be selected in accordance with the application case. Besides the schematically illustrated oval shapes, also round shapes or polygonal shapes of windings are possible, for example. The size of the absolute coil arrangements, i.e. their lateral extension in the circumferential direction, can be adapted to the individual case. As shown in FIG. 5, the extension of the absolute coil arrangements in circumferential direction can be significantly smaller than that of the differential coil arrangements, which are to complement one another in total over a plurality of shells in circumferential direction to a complete overlapping and to a detection of the complete circumference of the test specimen, respectively. That is not required in the case of the absolute coil arrangements and it is in general also not desired. For exact determination of the distance without interference due to flaws in the material surface, very short lengths in circumferential direction, where appropriate even almost point-shaped distance sensors, may be favorable. However, a certain physical extension is desired so that the voltages induced in the loops are sufficiently great for reliable evaluation.

In a typical embodiment, segmented absolute coil arrangements are present in circumferential direction, wherein each absolute coil arrangement covers only a part of the circumference of the test specimen. Generally, the absolute coil arrangements do not overlap in the circumferential direction. The absolute coil arrangements serve as distance sensors. Here, a separate absolute coil surrounding the long product for flaw detection is not provided.

Optionally, a parametric detection of a standard absolute signal over the entire circumference of the feed-through coil arrangement by means of the exciter coil 122 may be provided. Here, the exciter coil acts as parametric absolute coil, wherein the excitation and the detection is effected by means of the same component and the impedance change is evaluated.

In other embodiments, an absolute coil separate from the segment coil arrangements and the exciter coil arrangement and surrounding the long product, may be provided.

In addition to the embodiments discussed in detail, a multitude of variants is possible within the scope of the invention. For example, a feed-through coil arrangement may comprise more than two shells with differential coil arrangements. It is possible that a feed-through coil arrangement operates without absolute coil arrangements and only with differential coil arrangements. It is also possible to combine segment coil arrangements not having an absolute coil arrangement and segment coil arrangements having absolute coil arrangements.

If only a determination of the diameter, diameter shape, diameter fluctuation and/or eccentricity of the position of the test specimen when being fed through is desired, the feed-through coil arrangement could be made of and/or used even without differential coil arrangements, i.e. only with segmented absolute coil arrangements. A complete defect testing or a defect testing optimized for certain flaw types could then be conducted by means of a separate test apparatus, where appropriate.

Here, in addition to the assessment of the fault signal, also or only a mechanical correction of the position of the long product could be effected by means of the data obtained.

Figure 6:
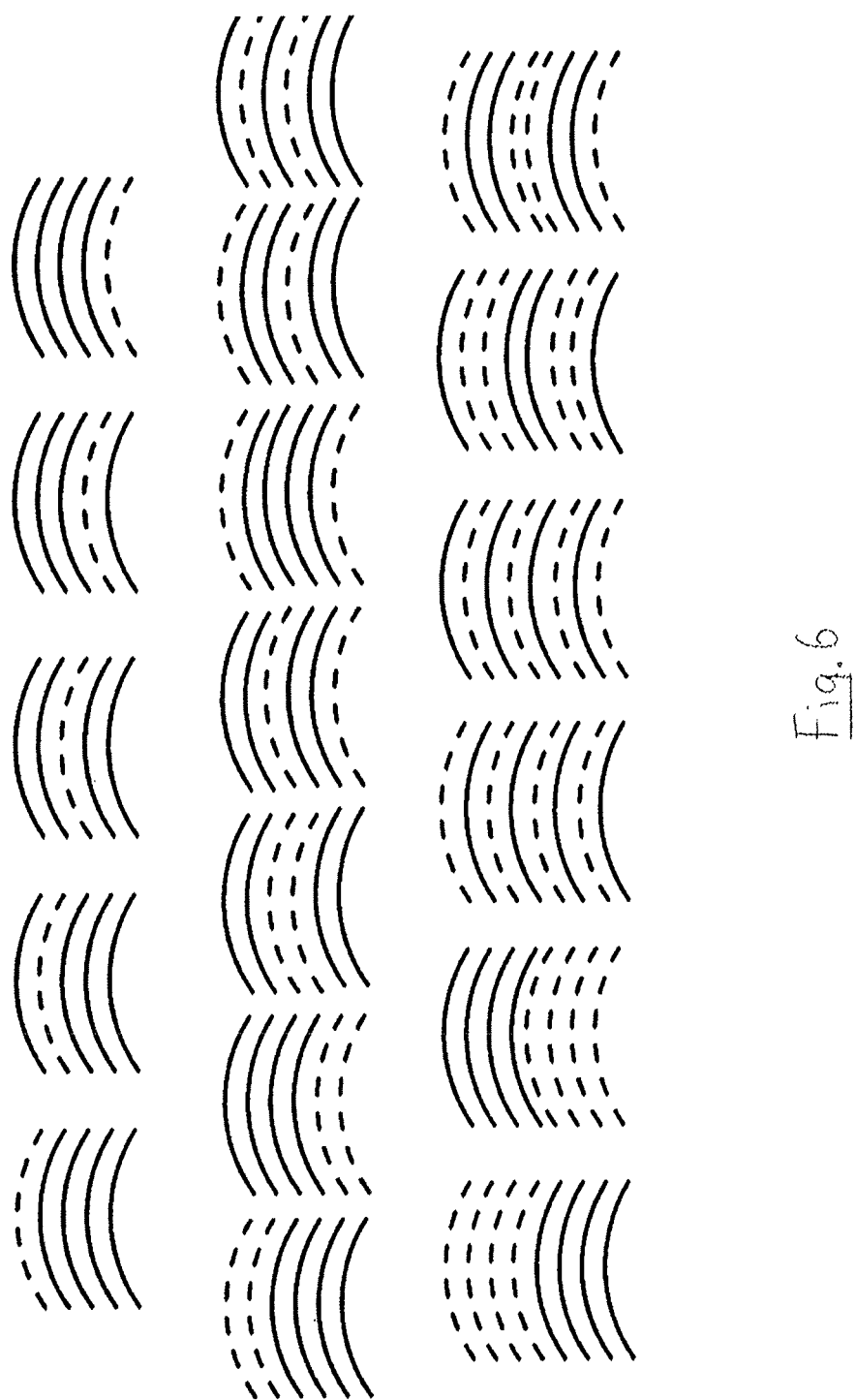
FIG. 6 shows different variants of shell arrangements with differential and absolute coil arrangements.

In an exemplary manner, FIG. 6 shows several variants, where in each case four shells having differential coil arrangements are combined to one or a plurality of shells having absolute coil arrangements. Here, the use of absolute coils allows a distance compensation, where required. In this case, the solid lines represent shells only comprising differential coil arrangements. The dashed lines represent shells only comprising absolute coil arrangements for distance detection. As already explained with regard to FIG. 5, absolute coil arrangements and differential coil arrangements do not have to be located on different shells, but can also be located on one shell having the same distance to the central axis. As a result of the knowledge of the characteristic distance performance of both differential channels and distance channels, it is possible by means of suitable hardware components and by means of suitable evaluation software, to achieve a compensation of the different sensitivity performance in flaw detection which is based on an eccentricity of the long product.

The invention is not limited to feed-through coil arrangements having a circular cross-section. FIG. 7 shows an exemplary embodiment of a non-round, shape-adjusted feed-through coil arrangement 700, which is configured for testing of long products having a rectangular cross-section, in particular having a square-shaped cross-section. Components and features of similar or the same function as in FIG. 2 have the same reference symbols, increased by 600.

The exciter coil 722 and the shells S1 and S2 have in each case an approximately square-type shape with rounded corners. The four plane segment coil arrangements 742-5 to 742-8 of the outer second shell S2 test the plane side faces of the long product up to the vicinity of the longitudinal edges. The edge regions are detected by the first segment coil arrangements 742-1 to 742-4 of the inner first shell S1. Said arrangements are configured in an angular manner, wherein an arcuately curved central section is located between the arms that are arranged perpendicular (90°) to one another. The electric connections and the evaluation options are analog to those of the first exemplary embodiment.

As already mentioned, square-type and other polygonal cross-sections (e.g. hexagonal bar) can in some cases also be tested by means of a circular arrangement of segmented coils (see for example FIG. 1, 2).

The invention claimed is:

1. A feed-through coil arrangement for use in a test apparatus for testing long products in a feed-through method by use of eddy current, comprising:
   an exciter coil arrangement with an exciter coil which surrounds a passage opening for feeding-through a long product along a feed-through direction, wherein the exciter coil arrangement comprises a connection device for connecting the exciter coil to an alternating current source; and
   a receiver coil arrangement arranged around the passage opening, which comprises a connection device for connecting the receiver coil arrangement to an evaluation device of the test apparatus, wherein
   the receiver coil arrangement comprises two or more segment coil arrangements distributed over the circumference of the passage opening, wherein each segment coil arrangement has a detection range that only covers a circumferential section of the circumference of the surface of the long product,
   the segment coil arrangements are distributed over at least two shells surrounding the passage opening at different distances to a reference axis of the feed-through coil arrangement,
   first segment coil arrangements are arranged on a first shell without reciprocal overlapping,
   second segment coil arrangements are arranged on a second shell without reciprocal overlapping, and the first and second segment coil arrangements are arranged circumferentially offset to one another in circumferential direction such that the second segment coil arrangements detect circumferential sections that are not covered by the first segment coil arrangements.

2. The feed-through coil arrangement according to claim 1, wherein the first segment coil arrangements are arranged at a first radial distance to a central reference axis on a circular-cylindrical first shell and the second segment coil arrangements are arranged at a second radial distance to the central reference axis different from the first radial distance on a circular cylindrical second shell.

3. The feed-through coil arrangement according to claim 1, wherein the shells have a cross-sectional shape deviating from a circular shape.

4. The feed-through coil arrangement according to claim 1, wherein the shells have one of: an oval cross-sectional shape, an egg-shaped cross-sectional shape, and a square-shaped cross-sectional shape with rounded corner ranges.

5. The feed-through coil arrangement according to claim 1, wherein on each shell, an even number of segment coil arrangements is arranged.

6. The feed-through coil arrangement according to claim 1, wherein on one or more shells, at least one pair of diametrically opposite segment coil arrangements is provided.

7. The feed-through coil arrangement according to claim 1, wherein all segment coil arrangements in each case comprise a differential coil arrangement, wherein the differential coil arrangements are arranged such that differential signals are detectable on the entire circumference of the long product.

8. The feed-through coil arrangement according to claim 1, wherein a segment coil arrangement comprises a differential coil arrangement and an absolute coil arrangement.

9. The feed-through coil arrangement according to claim 8, wherein the differential coil arrangement and the absolute coil arrangement are attached to a common support element, wherein the common support element comprises an inner surface and an outer surface and the differential coil arrangement and the absolute coil arrangement are arranged at a same surface of the support element.

10. The feed-through coil arrangement according to claim 8, wherein in a segment coil arrangement, the differential coil arrangement is symmetrically arranged to a coil plane of the exciter coil arrangement and the absolute coil arrangement is arranged unsymmetrically to the coil plane and at least partially in an inhomogeneous field region of a field generated by the exciter coil arrangement.

11. The feed-through coil arrangement according to claim 8, wherein an absolute coil arrangement comprises, symmetrically to a coil plane of the exciter coil arrangement in a first inhomogeneous field region in front of the coil plane, a first partial coil arrangement and, in a second inhomogeneous field region behind the coil plane, a second partial coil arrangement, wherein the first and the second partial coil arrangements are connected in opposite directions.

12. The feed-through coil arrangement according to claim 8, wherein a plurality of circumferentially offset absolute coil arrangements are connected to a distance evaluation device for processing of a distance signal generated on an absolute coil arrangement.

13. The feed-through coil arrangement according to claim 1, wherein the exciter coil is a flat ribbon coil having one single winding.

14. A test apparatus for testing long products which are moved along a feed-through direction through a feed-through coil arrangement, wherein the test apparatus comprises the feed-through coil arrangement according to claim 1.

15. A test method for testing long products, the method comprising the acts of:
a) moving a long product along a feed-through direction through a feed-through coil arrangement having an exciter coil arrangement with an exciter coil which surrounds a passage opening for feeding-through the long product along the feed-through direction, wherein the exciter coil arrangement comprises a connection device for connecting the exciter coil to an alternating current source; and a receiver coil arrangement arranged around the passage opening, which comprises a connection device for connecting the receiver coil arrangement to an evaluation device of the test apparatus, wherein
the receiver coil arrangement comprises two or more segment coil arrangements distributed over the circumference of the passage opening,
the segment coil arrangements are distributed over at least two shells surrounding the passage opening at different distances to a reference axis of the feed-through coil arrangement,
first segment coil arrangements are arranged on a first shell without reciprocal overlapping,
second segment coil arrangements are arranged on a second shell without reciprocal overlapping, and
the first and second segment coil arrangements are arranged circumferentially offset to one another in circumferential direction,
b) detecting, by use of eddy current, only circumferential sections of a circumference of a surface of the long product via the respective first and second segment coil arrangements, wherein the second segment coil arrangements detect circumferential sections that are not covered by the first segment coil arrangements.

16. The test method according to claim 15, further comprising the act of:
commonly evaluating absolute signals of pairwise diametrically opposed segment coil arrangements, wherein the act of commonly evaluating comprises determining a sum signal of absolute signals and/or differential signals of the pairwise diametrically opposite segment coil arrangements.

17. The test method according to claim 16, further comprising at least one of the following acts:
(i) using absolute signals of a plurality of absolute coil arrangements distributed over the circumference for distance compensation, and
(ii) determining information regarding diameter, test specimen geometry, out-of-roundness and/or axis offset between the feed-through coil arrangement and the test object from absolute signals of a plurality of absolute coil arrangements distributed over the circumference.

18. The test method according to claim 15, further comprising at least one of the following acts:
(i) using absolute signals of a plurality of absolute coil arrangements distributed over the circumference for distance compensation, and
(ii) determining information regarding diameter, test specimen geometry, out-of-roundness and/or axis offset between the feed-through coil arrangement and the test object from absolute signals of a plurality of absolute coil arrangements distributed over the circumference.

* * * * *